(12) United States Patent
Wronska et al.

(10) Patent No.: US 10,113,206 B2
(45) Date of Patent: Oct. 30, 2018

(54) METHODS, COMPOSITIONS, AND KITS FOR DETERMINING HUMAN IMMUNODEFICIENCY VIRUS (HIV)

(71) Applicant: GRIFOLS THERAPEUTICS INC., Research Triangle Park, NC (US)

(72) Inventors: Danuta Wronska, Raleigh, NC (US); Terri W Journigan, Wendell, NC (US); James D Mellott, Raleigh, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 845 days.

(21) Appl. No.: 14/221,341

(22) Filed: Mar. 21, 2014

(65) Prior Publication Data

US 2015/0267268 A1 Sep. 24, 2015
US 2017/0204480 A9 Jul. 20, 2017

Related U.S. Application Data

(63) Continuation of application No. 13/033,507, filed on Feb. 23, 2011, now abandoned.

(60) Provisional application No. 61/307,646, filed on Feb. 24, 2010.

(51) Int. Cl.
*C12Q 1/70* (2006.01)

(52) U.S. Cl.
CPC ........ *C12Q 1/703* (2013.01); *C12Q 2600/112* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,415,732 A | 11/1983 | Caruthers et al. | |
| 4,458,066 A | 7/1984 | Caruthers et al. | |
| 4,605,735 A | 8/1986 | Miyoshi et al. | |
| 4,757,141 A | 7/1988 | Fung et al. | |
| 4,826,967 A | 5/1989 | Glass et al. | |
| 4,965,188 A | 10/1990 | Mullis et al. | |
| 5,082,934 A | 1/1992 | Saba et al. | |
| 5,389,512 A | 2/1995 | Kwok et al. | |
| 5,399,491 A | 3/1995 | Kacian et al. | |
| 5,908,743 A * | 6/1999 | Christopherson | C12Q 1/703 435/5 |
| 6,030,769 A * | 2/2000 | Simon | C07K 14/005 424/160.1 |
| 6,270,975 B1 | 8/2001 | Simon et al. | |
| 6,531,276 B1 | 3/2003 | Luciw et al. | |
| 6,534,273 B2 | 3/2003 | Weisburg et al. | |
| 6,965,020 B2 | 11/2005 | McGall et al. | |
| 9,273,366 B2 * | 3/2016 | Wronska | C12Q 1/703 |
| 2003/0050470 A1 * | 3/2003 | An | C07H 21/00 536/24.3 |
| 2005/0181439 A1 * | 8/2005 | Choi | C07K 14/3156 435/6.15 |
| 2007/0015180 A1 | 1/2007 | Sorge | |
| 2010/0136631 A1 | 6/2010 | Tcherepanova | |

FOREIGN PATENT DOCUMENTS

| | | | |
|---|---|---|---|
| CN | 1940087 A | 4/2007 | |
| WO | WO 2009135832 A1 * | 11/2009 | ........... C12Q 1/6818 |
| WO | WO 2012174187 A2 * | 12/2012 | ............. C12Q 1/703 |

OTHER PUBLICATIONS

Grassly et al. Journal of Virology 1998; 72: 7895-7899.*
GenBank Accession No. AJ011222 for the human immunodeficiency virus type 2 gag gene, isolate b1276 (Jul. 25, 2016) [online], [retrieved on Apr. 18, 2017], retrieved from the Internet: <URL: www.ncbi.nlm.nih.gov/nuccore/aj011222>.*
Markoulatos et al. Journal of Clinical Laboratory Analysis 2002; 16: 47-51.*
Marras, S.A.E. Molecular Biotechnology 2008; 38: 247-255.*
Abravaya et al. Journal Clinical Microbiology 2000; 38: 716-723 (Year: 2000).*
Broker, T., et al., "Electron Microscopic Visualization of tRNA Genes with Ferritin-Avidin: Biotin Labels," Nucl. Acids Res. 5:363-384 (1978).
Chollet, A. and E. H. Kawashima, "Biotin-Labeled Synthetic Oligodeoxyribonucleotides: Chemical Synthesis and Uses and Hybridization . . . " Nucl. Acids Res. 13:1529-1541 (1985).
Compton, J., "Nucleic Acid Sequence-Based Amplification," Nature 350:91-92 (1991).
Connolly, B.A. "Chemical Synthesis of Oligonucleotides Containing a Free Sulphydryl Group and Subsequent Attachment of Thiol Specific . . . " Nucl. Acids Res. 13:4485-4502 (1985).
Connolly, B.A., "The Synthesis fo Olognucleotides Containing a Primary Amino Group at the 5'-Terminus," Nucl. Acids Res. 15:3131-3139 (1987).
Lowe et al.. "A Computer program for selection of oligonucleotide primers for polymerase chain reactions," Nucl. Acids Res. 18(7):1757-1761 (1990).
Xiang et al. "HIV Type 2 Pathogenecity is not related to subtype in Rural Guinea Bissau," AIDS Res. and Human Retroviruses 13(6):501-505 (1997).

* cited by examiner

*Primary Examiner* — Angela M. Bertagna
(74) *Attorney, Agent, or Firm* — Womble Bond Dickinson (US) LLP

(57) ABSTRACT

The present invention relates to compositions, methods, and kits for determining the presence or absence of HIV in a sample, in particular for determining HIV-1 group M, HIV-1 group O, and/or HIV-2, in particular for simultaneous determining of HIV-1 group M, HIV-1 group O, and HIV-2.

7 Claims, No Drawings
Specification includes a Sequence Listing.

METHODS, COMPOSITIONS, AND KITS FOR DETERMINING HUMAN IMMUNODEFICIENCY VIRUS (HIV)

CROSS REFERENCE TO RELATED APPLICATIONS

This application is a continuation of U.S. patent application Ser. No. 13/033,507, filed on Feb. 23, 2011, now abandoned, which claims benefit of priority under 35 U.S.C. § 119 to U.S. Provisional Patent Application No. 61/307,646, filed Feb. 24, 2010, each of which are incorporated by reference herein in their entirety.

TECHNICAL FIELD

The present invention relates to HIV and includes methods, compositions, and kits for detecting same.

BACKGROUND

Some of the assays that detect different HIV genetic variants require separate test runs for their detection. For example, most PCR methods currently available for detection of HIV do not detect HIV type 2 (HIV-2).

Some of the assays that detect different HIV genetic variants require separate test runs for their detection. For example, most PCR methods currently available for detection of HIV do not detect HIV type 2 (HIV-2).

Multiplex real time PCR is a type of PCR configured to detect multiple targets (e.g., pathogens or genetic variations of a pathogen) in a single test tube with a combination of PCR reagents in a single test run. This is attempted by introducing a set of primers and probes specific for each target into one PCR master mix. However, providing primers and probes that work effectively together and provide efficient amplification and detection of all desired targets is challenging due to several factors, including competition between amplified targets and undesirable interactions between primers called primer-dimer formation.

There is still a need, therefore, for compositions and methods for detecting HIV.

SUMMARY

There is now provided, in one aspect, an isolated nucleic acid molecule comprising a nucleotide sequence, or a complement thereof, as set forth in:

```
                                       (SEQ ID NO: 1)
5'-GAC ATC AAG CAG CCA TGC AAA T-3';

(SEQ ID NO: 2)
5'-AGT AGT TCC TGC TAT GTC ACT TC-3';

(SEQ ID NO: 3)
5'-GAG GAC ATC AAG GGG CTT TAC A-3';

(SEQ ID NO: 4)
5'-CAG CAA TGT CAC TTC CTG TTG-3';

(SEQ ID NO: 5)
5'-GGC AGA GGT AGT GCC AG-3';

(SEQ ID NO: 6)
5'-GGT CGC CCA CAC AAT TAA GC-3';

(SEQ ID NO: 7)
5'-ACC ATC AAT GAG GAA GCT GCA GAA TGG GAT-3';

(SEQ ID NO: 8)
5'-TCC CTT ATC TGC CCT GGT GGT AAC GG-3';
or
                                       (SEQ ID NO: 9)
5'-AGG CAC TCT CAG AAG GCT GCA CG-3'.
```

In another aspect, the present invention provides a composition comprising a pair of oligonucleotide primers comprising a first primer having a sequence as set forth in SEQ ID NO:1 and a reverse primer having a sequence as set forth in SEQ ID NO:2, wherein the pair of primers are capable of annealing to a target sequence under a PCR condition to amplify the target sequence.

In some aspects, the present invention provides a composition comprising a pair of oligonucleotide primers comprising a first primer having a sequence as set forth in SEQ ID NO:3 and a reverse primer having a sequence as set forth in SEQ ID NO:4, wherein the pair of primers are capable of annealing to a target sequence under a PCR condition to amplify the target sequence.

In other aspects, the present invention provides a composition comprising a pair of oligonucleotide primers comprising a first primer having a sequence as set forth in SEQ ID NO:5 and a reverse primer having a sequence as set forth in SEQ ID NO:6, wherein the pair of primers are capable of annealing to a target sequence under a PCR condition to amplify the target sequence.

In one aspect, the present invention provides a composition comprising a first pair of oligonucleotide primers comprising a first primer having a sequence as set forth in SEQ ID NO:1 and a reverse primer having a sequence as set forth in SEQ ID NO:2, a second pair of oligonucleotide primers comprising a second primer having a sequence as set forth in SEQ ID NO:3 and a second reverse primer having a sequence as set forth in SEQ ID NO:4, a third pair of oligonucleotide primers comprising a third primer having a sequence as set forth in SEQ ID NO:5 and a third reverse primer having a sequence as set forth in SEQ ID NO:6, wherein each pair of primers are capable of annealing to a target sequence under a PCR condition to amplify the target sequence.

In another aspect, the present invention provides a method for amplifying a target sequence, the method comprising:
performing a PCR with the target sequence as template, wherein performing comprises providing the PCR with a forward primer comprising the sequence as set forth in SEQ ID NO:1 and a reverse primer comprising the sequence as set forth in SEQ ID NO:2.

In some aspects, the present invention provides a method for amplifying a target sequence, the method comprising:
performing a PCR with the target sequence as template, wherein performing comprises providing the PCR with a forward primer comprising the sequence as set forth in SEQ ID NO:3 and a reverse primer comprising the sequence as set forth in SEQ ID NO:4.

In other aspects, the present invention provides a method for amplifying a target sequence, the method comprising:
performing a PCR with the target sequence as template, wherein performing comprises providing the PCR with a forward primer comprising the sequence as set forth in SEQ ID NO:5 and a reverse primer comprising the sequence as set forth in SEQ ID NO:6.

In one aspect, the present invention provides a method for determining HIV in a sample, the method comprising:
performing a PCR with a nucleic acid template in the sample using a forward primer comprising the sequence as set forth in SEQ ID NO:1 and a reverse primer comprising the sequence as set forth in SEQ ID NO:2; and detecting an amplicon generated by the forward and the reverse primer, wherein the presence of the amplicon determines the HIV in the sample.

In another aspect, the present invention provides a method for determining HIV in a sample, the method comprising:

performing a PCR with a nucleic acid template in the sample using a forward primer comprising the sequence as set forth in SEQ ID NO:3 and a reverse primer comprising the sequence as set forth in SEQ ID NO:4; and detecting an amplicon generated by the forward and the reverse primer, wherein the presence of the amplicon determines the HIV in the sample.

In some aspects, the present invention provides a method for determining HIV in a sample, the method comprising:

performing a PCR with a nucleic acid template in the sample using a forward primer comprising the sequence as set forth in SEQ ID NO:5 and a reverse primer comprising the sequence as set forth in SEQ ID NO:6; and detecting an amplicon generated by the forward and the reverse primer, wherein the presence of the amplicon determines the HIV in the sample.

In other aspects, the present invention provides a method for determining HIV-1 group M, HIV-1 group O, and/or HIV-2 in a sample, the method comprising:

performing a single PCR with a nucleic acid template in the sample using (i) a first forward primer comprising the sequence as set forth in SEQ ID NO:1 and a first reverse primer comprising the sequence as set forth in SEQ ID NO:2; (ii) a second forward primer comprising the sequence as set forth in SEQ ID NO:3 and a second reverse primer comprising the sequence as set forth in SEQ ID NO:4; and (iii) a third forward primer comprising the sequence as set forth in SEQ ID NO:5 and a third reverse primer comprising the sequence as set forth in SEQ ID NO:6; and detecting an amplicon generated by (i) the first forward and the first reverse primers, (ii) the second forward and the second reverse primers, and/or (iii) the third forward and the third reverse primers, wherein the presence of the amplicon determines the HIV in the sample.

In still further aspects, the present invention provides a kit comprising the compositions and/or the one or more of the nucleic acid molecules of the present invention.

DETAILED DESCRIPTION

There is now provided, in one aspect, an isolated nucleic acid molecule comprising a nucleotide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or a complement thereof.

In one embodiment, the present invention provides an isolated nucleic acid molecule comprising a nucleotide sequence as set forth in SEQ ID NO:2, SEQ ID NO:3, SEQ ID NO:4, SEQ ID NO:5, SEQ ID NO:6, SEQ ID NO:8, or a complement thereof.

In some embodiments, the isolated nucleic acid molecules of the present invention have a length of no more than about 100 base pairs, illustratively, no more than about: 100, 90, 80, 70, 60, 55, 50, 45, 40, 35, 34, 33, 32, 31, 30, 29, 28, 27, 26, 25, 24, 23, 22, 21, 20, 19, 18, 17, 16, 15, 14, 13, 12, 11, and 10 bps.

In other embodiments, the present invention provides an isolated nucleic acid molecule comprising a nucleotide sequence as set forth in SEQ ID NO:1, or a complement thereof, wherein the isolated nucleic acid molecule is no more than about 29 base pairs in length. In one embodiment, the isolated nucleic acid molecule is no more than about 22 base pairs in length.

In still further embodiments, the present invention provides an isolated nucleic acid molecule comprising a nucleotide sequence as set forth in SEQ ID NO:7, or a complement thereof, wherein the isolated nucleic acid molecule is no more than 32 base pairs in length. In one embodiment, the isolated nucleic acid molecule is no more than about 23 base pairs in length.

In another embodiment, the present invention provides an isolated nucleic acid molecule consisting of or consisting essentially of a nucleotide sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or a complement thereof.

The term "nucleic acid molecule" herein includes polymers composed of naturally occurring nucleotide bases, sugars and covalent internucleoside (backbone) linkages as well as nucleic acid molecules having non-naturally-occurring portions that function similarly. Further, the term "nucleic acid molecule" also includes polymers that are double-stranded, single-stranded, comprising RNA, DNA, modified RNA or DNA, RNA or DNA mimetics, or any combination thereof.

In some embodiments, oligonucleotide primers and probes can be derived from the nucleic acid sequences disclosed herein. In various embodiments, primers and probes are used in combination with each other. The present invention finds use in a variety of different applications including, but not limited to, research, medical, and diagnostic applications for HIV. For example, the primers and probes can provide for reagents for use in, for example, an HIV detection assay or kit thereby expanding the repertoire of HIV variants that can be detected by the assay or kit.

Generally, a pair of primers comprising a forward primer and a reverse primer can provide for specific amplification (e.g., by PCR) of a target nucleic acid flanked by the primers to produce an amplification product (also referred to as an "amplicon"). In this regard, each primer binds to its complementary or substantially complementary target sequence thereby providing a place for a polymerase to bind and extend each primer's 3'-end by the addition of nucleotides thereby providing a complementary copy of the target sequence.

In one embodiment, a primer pair comprises a forward primer having the sequence as set forth in SEQ ID NO:1 and a reverse primer having the sequence as set forth in SEQ ID NO:2.

In another embodiment, a primer pair comprises a forward primer having the sequence as set forth in SEQ ID NO:3 and a reverse primer having the sequence as set forth in SEQ ID NO:4.

In other embodiments, a primer pair comprises a forward primer having the sequence as set forth in SEQ ID NO:5 and a reverse primer having the sequence as set forth in SEQ ID NO:6.

In one embodiment, the target nucleic acid is at least a segment of a cDNA prepared from reverse transcribed RNA of an HIV (e.g., HIV-1 group M, HIV-1 group O, HIV-2).

One of ordinary skill in the art will recognize that RNA can be reverse transcribed using methods known in the art to provide a template for amplification by primers.

In another embodiment, the target nucleic acid is at least a segment of an HIV (e.g., HIV-1 group M, HIV-1 group O, HIV-2) proviral DNA integrated into the DNA of a host cell (e.g., T-lymphocyte, macrophage, dendritic cell). Preparing cellular DNA including proviral DNA is known in the art.

Generally, a probe is an oligonucleotide that is complementary or substantially complementary to a nucleotide sequence of the target nucleic acid. Probes are useful for a variety of applications including, but not limited to, detecting or capturing the target nucleic acid or an amplicon corresponding to the target. For example, probes suitable for use in amplification-based detection methods can be designed from any sequence positioned within and/or comprising the sequence of an amplification product that would be produced using two selected primers.

In one embodiment, the probe comprises a nucleotide sequence complementary to or substantially complementary to at least a portion of a sequence of an amplicon generated by a primer pair comprising a forward primer having the sequence as set forth in SEQ ID NO:1 and a reverse primer having the sequence as set forth in SEQ ID NO:2.

In another embodiment, the probe comprises a nucleotide sequence complementary to or substantially complementary to at least a portion of a sequence of an amplicon generated by a primer pair comprising a forward primer having the sequence as set forth in SEQ ID NO:3 and a reverse primer having the sequence as set forth in SEQ ID NO:4.

In some embodiments, the probe comprises a nucleotide sequence complementary to or substantially complementary to at least a portion of a sequence of an amplicon generated by a primer pair comprising a forward primer having the sequence as set forth in SEQ ID NO:5 and a reverse primer having the sequence as set forth in SEQ ID NO:6.

In other embodiments, the probe comprises the nucleotide sequence as set forth in SEQ ID NO:7, SEQ ID NO:8, SEQ ID NO:9, or a complement thereof.

One skilled in the art will recognize that the isolated nucleic acid molecules of the present invention including primers and/or probes can be obtained by standard molecular biology techniques described in *Current Protocols in Molecular Biology* (1999) Ausubel F M, Brent R, Kingston R E, Moore D D, Seidman J G, Smith J A, Struhl K, editors. John Wiley & Sons, Inc. or by chemical synthesis or by nucleic acid analogs. Methods involving chemical synthesis may be automated and commercially available and can include, for example, phosphodiester, phosphotriester, or phosphoramidite methods. U.S. Pat. Nos. 4,458,066; 4,415,732; and *Meth. Enzymol.* 1979 68:90 and 109, which are incorporated herein by reference, disclose examples of chemical synthesis methods. Chemical nucleic acid synthesis allows for the incorporation of unnatural or modified bases, as well as a variety of labeling moieties, into a nucleic acid molecule. Further, modified backbone chemistries such as, for example, peptide linkages, phosphorothioates, phosphoramidates, phosphotriesters, 2'-O-Methyl RNA, 2'-O-Mt RNA, P-Ethoxy DNA, and P-Ethoxy 2'-O-Mt RNA are also readily available and known in the art. Furthermore, the uses of cross-linkable probes in nucleic acid hybridization assays to cross-link to target sequences are known in the art. For example, compounds based on furocoumarin or psoralen attached to nucleic acid molecules through adduct formation are described in U.S. Pat. No. 4,826,967 and U.S. Pat. No. 5,082,934, both incorporated herein by reference, describes a photoactivatable nucleoside analogue comprising a coumarin moiety linked through its phenyl ring to the 1-position of a ribose or deoxyribose sugar moiety in the absence of an intervening base moiety.

Nucleic acid analogs and mimics have similar chemical structures as native nucleic acid molecules but with unique modifications. Nucleic acid analogs, such as locked nucleic acids (LNAs), peptide nucleic acids (PNAs), and morpholinos, improve the capabilities of traditional nucleic acid molecules beyond the limitations associated with standard nucleic acids chemistry. Karkare S and Bhatnagar D. *Appl. Microbiol. Biotechnol.* 71:575-586 (2006). Such nucleic acid analogs greatly expand and improve the capabilities to detect and identify related nucleic acid sequences.

In some aspects, an isolated nucleic acid molecule of the present invention further comprises one or more heterologous nucleotides. The term "heterologous nucleotides" herein refers to a nucleotide or nucleotides that are not a natural part of the isolated nucleic acid molecule but which are naturally or artificially joined to the isolated nucleic acid molecule. Examples of a heterologous nucleic acid sequence include, but is not limited to, a vector sequence, a sequence that is complementary to a base sequence of a purification probe, and a sequence comprising one or more restriction enzyme sites.

In one embodiment, the one or more heterologous nucleotides comprise a sequence that is complementary to a base sequence of a purification probe. The purification probe can be joined to solid supports such as, for example, a matrix or particles free in solution. Non-limiting examples of a solid support include nitrocellulose, nylon, glass, polyacrylate, mixed polymers, polystyrene, silane polypropylene, and magnetically attractable particles. For example, the purification probe, which may comprise a DNA or RNA sequence, can be labeled with amine or biotin tags via a cross-linker. These biotin or amine labeled purification probes are then amenable to immobilization and detection strategies that allow in vitro nucleic acid:nucleic acid or protein:nucleic acid interactions. Thus, annealing of the heterologous segment of the isolated nucleic acid molecule with its complementary base sequence of the purification probe can facilitate sample purification of molecules that anneal virus-specific sequence segment of the isolated nucleic acid molecule. U.S. Pat. No. 6,534,273, incorporated herein by reference, describes a method for capturing a target nucleic acid molecule in a sample onto a solid support.

In one embodiment, the isolated nucleic acid molecules of the present invention are joined to a solid support such as those described above.

In some embodiments, the one or more heterologous nucleotides comprise one or more repeating base sequences, for example, one or more repeating base sequences that are complementary to one or more repeating base sequences of the purification probe. A repeating base sequences can be a regularly repeating base sequence, such as those formed, for example, by nucleic acid homopolymers of poly-adenine ($A_n$), poly-thymine ($T_n$), poly-cytosine (CO, poly-guanine ($G_n$), and poly-uridine ($U_n$). Repeating sequences also can include mixed polymers, such as AT repeats ($[AT]_n$), and the like.

The number of bases of the repeating base sequence of the one or more heterologous nucleotides of the isolated nucleic acid molecule can be equal to, greater than, or less than the number of bases of the repeating base sequence of the purification probe. The lengths of the complementary repeating sequences can determine the melting temperature ($T_m$) of the heterologous segment:purification probe complex. In one embodiment, the repeating base sequence of the heterologous segment is longer than the complementary repeating base sequence of the purification probe. In another embodiment, the repeating base sequence of the heterologous segment or the purification probe can be at least about 5 bases in length, illustratively about 5 to about 40, about 10 to about 30, or about 15 to about 20, and the like.

In other embodiments, the one or more heterologous nucleotides comprise an operably linked control sequence. In one embodiment, the control sequence is an enhancer or a promoter sequence that is specifically recognized by an RNA polymerase that binds to that sequence and initiates transcription to produce RNA transcripts. Non-limiting examples of promoters recognized by an RNA polymerase include promoters such as T3, T7, or SP6. Thus, an isolated nucleic acid molecule can be used in a variety of nucleic acid based assays including assays that use an RNA polymerase to produce multiple RNA transcripts such as, for example, transcription-mediated amplification (TMA) assay as described in *Nature* 350:91-92 (1991); and U.S. Pat. No. 5,399,491, both incorporated herein by reference.

In one embodiment, the isolated nucleic acid sequences of the present invention are labeled, e.g., labeled radioactively, chemiluminescently, fluorescently, phosphorescently or with infrared dyes or with a surface-enhanced Raman label or plasmon resonant particle (PRP). For example, modifications of nucleotides include the addition of acridine or derivatives thereof, Acrydite™, amine, biotin, BHQ-1™, BHQ-2™, BHQ-3™, borane dNTPs, carbon spacers (e.g., C3, C6, C7, C9, C12 or C18), cascade blue, cholesterol, coumarin or derivatives thereof, Cy3®, Cy3.5®, Cy5®, Cy5.5®, Cy7® DABCYL, dansylchloride, digoxigenin, genin, dinitrophenyl, dual biotin, EDANS, 6-FAM, fluorescein, 3'-glyceryl, HEX, IAEDANS, inverted dA, inverted dG, inverted dC, inverted dG, IRD-700, IRD-800, JOE, La Jolla Blue, metal clusters such as gold nanoparticles, phenylboronic acid, phosphate psoralen, 3'- or 5'-phosphorylation, pyrene, 3' ribo-adenosine, 3' ribo-guanosine, 3' ribo-cytidine, (LC)Red640, (LC)Red705, rhodamine, ROX, thiol (SH), spacers, TAMRA, TET, AMCA-S®, SE, BODIPY®, Marina Blue®, Oregon Green®, Pacific Blue®, QSY7™, Rhodamine Green®, Rhodamine Red®, Rhodol Green®, tetramethylrhodamine, Texas Red®, Uni-Link NH2-modifier, radiolabels (e.g., $^{125}$I, $^{131}$I, $^{35}$S, $^{14}$C, $^{32}$P, $^{33}$P, $^{3}$H) and nanoparticles. A variety of labeling techniques are known to one of ordinary skill in the art.

Labels can be joined directly or indirectly to the isolated nucleic acid molecule. The labeling of a nucleic acid can be performed by covalently attaching a detectable group (label) to either an internal or a terminal position, for example. One skilled in the art knows that there are varieties of ways for derivatizing oligonucleotides with reactive functionalities that permit the addition of a label. A number of approaches are available for directly attaching labels to nucleic acid molecules and for biotinylating probes so that radioactive, fluorescent, chemiluminescent, enzymatic, or electron dense labels can be attached via avidin. Non-limiting examples of references describing labels and methods for labeling nucleic acids include U.S. Pat. No. 4,605,735; U.S. Pat. No. 4,757,141; U.S. Pat. No. 6,965,020; *Nucl. Acids Res.* 5:363 (1978); *Nucl. Acids Res.* 13:1529 (1985); *Nucl. Acids Res.* 15:3131 (1987); *Nucl. Acids Res.* 15:6455 (1987); *Nucl. Acids Res.* 13:4485 (1985); *Nucl. Acids Res.* 15:4837 (1987); and *Anal. Biochem.* 169:1-25 (1988), which are incorporated herein by reference for their disclosure relating to labeling of nucleic acids.

In some embodiments, the isolated nucleic acid molecules are labeled for detecting methods using fluorescence resonance energy transfer (FRET). FRET involves two dyes, a donor and acceptor dye. FRET can be detected by either fluorescence of the acceptor dye ("sensitized fluorescence") if said acceptor is itself fluorescent, or by quenching of the donor dye fluorescence if said acceptor is a quenching non-fluorescent dye. FRET can be delayed if the donor dye releases its fluorescence over time. This process is termed "TR-FRET" or "time-resolved FRET." Donor and acceptor dyes can also be the same in which case FRET is detected by the resulting fluorescence depolarization. Dyes can also be covalently coupled to form a tandem fluorescent dye or tandem dye or tandem conjugate. For example, a single donor dye is then capable of exciting two acceptor dyes simultaneously, leading to the emission of light of multiple wavelengths. Preferably, the donor emission wavelength profile should at least partially overlap with the acceptor absorption wavelength profile.

Fluorescent dyes that can be employed include, but are not limited, BODIPY FL, Cy3®, Cy3.5®, Cy5®, Cy5.5®, EDANS, FAM, fluorescein, HEX, IAEDANS, JOE, Oregon Green®, (LC)Red640, (LC)Red705, ROX, TAMRA, TET, tetramethylrhodamine and Texas Red®.

Quencher dyes include, but are not limited to, BHQ-1™, BHQ-2™, BHQ-3™, DABCYL, metal clusters such as gold nanoparticles and QSY7™.

Donor/acceptor pairs that can be employed include, but are not limited to, FAM/BHQ-1, TET/BHQ-1, JOE/BHQ-1, HEX/BHQ-1, Oregon Green/BHQ-1, TAMRA/BHQ-2, ROX/BHQ-2, Cy3/BHQ-2, Cy3.5/BHQ-2, Texas Red/BHQ-2, Texas Red/BHQ-2, Cy5/BHQ-3, Cy5.5/BHQ-3 fluorescein/tetramethylrhodamine, fluorescein/fluorescein, fluorescein/QSY7, fluorescein/LC RED640, fluorescein/LC Red705 IAEDANS/fluorescein, EDANS/DABCYL, and BODIPY FLI/BODIPY FL.

In one embodiment, the present invention provides an isolated nucleic acid molecule comprising a nucleotide sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or a complement thereof, wherein the nucleic acid molecule further comprises a detectable label.

In another embodiment, the isolated nucleic acid molecule comprising a nucleotide sequence as set forth in SEQ ID NO:7, SEQ ID NO:8, SEQ ID NO:9, or a complement thereof, wherein the nucleic acid molecule further comprises a detectable label.

In some embodiments, the detectable label corresponds to a donor/acceptor pair suitable for detecting using FRET.

In other embodiments, the donor/acceptor pair is FAM/BHQ-1.

In still further embodiments, the present invention provides an isolated nucleic acid molecule comprising a nucleotide sequence as set forth in SEQ ID NO:7, SEQ ID NO:8, SEQ ID NO:9, or a complement thereof, wherein the nucleic acid molecule comprises FAM at the 5'-end and BHQ-1 at the 3'-end.

In one embodiment, the present invention provides a set of oligonucleotide probes comprising a first probe having the sequence as set forth in SEQ ID NO:7 or a complement thereof, and a second probe having the sequence as set forth in SEQ ID NO:8 or a complement thereof, wherein each probe comprises a different detectable label corresponding to a donor/acceptor pair suitable for detecting using FRET.

In another embodiment, the present invention provides a set of probes comprising a first probe having the sequence as set forth in SEQ ID NO:7 or a complement thereof, and a second probe having the sequence as set forth in SEQ ID NO:9 or a complement thereof, wherein each probe comprises a different detectable label corresponding to a donor/acceptor pair suitable for detecting using FRET.

In other embodiments, the present invention provides a set of probes comprising a first probe having the sequence as set forth in SEQ ID NO:8 or a complement thereof, and a second probe having the sequence as set forth in SEQ ID NO:9 or a complement thereof, wherein each probe comprises a different detectable label corresponding to a donor/acceptor pair suitable for detecting using FRET.

In some embodiments, the present invention provides a set of probes comprising a first probe having the sequence as set forth in SEQ ID NO:7 or a complement thereof, a second probe having the sequence as set forth in SEQ ID NO:8 or a complement thereof, and a third probe having the sequence as set forth in SEQ ID NO:9 or a complement thereof, wherein each probe comprises a different detectable label corresponding to a different donor/acceptor pair suitable for detecting using FRET.

In other embodiments, the nucleic acid molecules of the present invention can provide for simultaneous use of two or more probes using donor-acceptor energy transfer whereby, e.g., molecular beacons are prepared that possess differently colored fluorophores, enabling assays to be carried out that simultaneously detect different targets in the same reaction. For example, multiplex assays can contain a number of different primer sets, each set enabling the amplification of a unique gene sequence from a different HIV, and a corresponding number of molecular beacons can be present, each containing a probe sequence specific for one of the amplicons, and each labeled with a fluorophore of a different color. The color of the resulting fluorescence, if any, identifies the HIV in the sample, and the number of amplification cycles required to generate detectable fluorescence provides a quantitative measure of the number of target organisms present. If more than one type of HIV is present in the sample, the fluorescent colors that occur identify which are present.

In other aspects, the present invention provides a composition comprising one or more of the isolated nucleic acid molecules of the present invention. In some embodiments, the composition is a buffered solution. In other embodiments, the composition is lyophilized.

In one embodiment, the composition comprises a pair of primers having the sequence as set forth in (SEQ ID NO:1/SEQ ID NO:2); (SEQ ID NO:3/SEQ ID NO:4); or (SEQ ID NO:5/SEQ ID NO:6). In some embodiments, the composition comprises two of the pair of primers. In other embodiments, the composition comprises all three pairs of oligonucleotides.

In one embodiment, the composition further comprises a probe having the sequence as set forth in SEQ ID NO:7, SEQ ID NO:8, SEQ ID NO:9, or a complement thereof. In some embodiments, the composition further comprises two or all three of the probes.

In another embodiment, a composition is provided comprising a first, a second, and a third pair of primers, wherein the first pair of primers has the sequence as set forth in (SEQ ID NO:1/SEQ ID NO:2), wherein the second pair of primers has the sequence as set forth in (SEQ ID NO:3/SEQ ID NO:4), wherein the third pair of primers has the sequence as set forth in (SEQ ID NO:5/SEQ ID NO:6). In one embodiment, the composition further comprises of a first, a second, and a third probe, wherein the first, the second, and the third probe each comprise a detectable label suitable for use in a multiplex real time PCR.

In one embodiment, the composition comprises, in addition to the one or more nucleic acid molecules of the present invention, additional reagents such as DNA polymerase, cofactors, and deoxyribonucleoside-5'-triphosphates in suitable concentrations to provide amplification of the target nucleic acid. By way of example, in some embodiments, wherein the composition is a PCR solution, the minimal amount of DNA polymerase can be at least about 0.5 units/100 µL of solution, illustratively, about 0.5 to about 25 units/100 µL of solution and about 7 to about 20 units/100 µL of solution. Other amounts may be useful for a given amplification reaction or system. The "unit" can be defined as the amount of enzyme activity required to incorporate 10 nmoles of total nucleotides (dNTPs) into an extending nucleic acid chain in 30 minutes at 74° C. By way of another example, in other embodiments, the amount of each primer used in amplification can be at least about 0.075 µmolar, illustratively, about 0.075 to about 2 µmolar, but other amounts may be useful for a given amplification reaction or system. By way of a still further example, in some embodiments, the amount of each dNTP in the solution can be about 0.25 to about 3.5 mmolar, but other amounts may be useful for a given amplification reaction or system.

In other aspects, the present invention provides a method for amplifying a target sequence corresponding to an HIV. For example, in some embodiments, the target sequence can be a cellular DNA comprising HIV proviral DNA or the target sequence can be cDNA prepared from RNA of the HIV. For example, performing a PCR with the target sequence, at least a forward primer, and a reverse primer each capable of annealing to the target sequence under a suitable PCR condition can provide for amplification of the target sequence.

In one embodiment, the present invention provides a method for amplifying a target sequence, the method comprising: performing a PCR with the target sequence as template, wherein performing comprises providing the PCR with a forward primer comprising the sequence as set forth in SEQ ID NO:1 and a reverse primer comprising the sequence as set forth in SEQ ID NO:2. In one embodiment, the target sequence corresponds to cDNA prepared from RNA of a sample comprising an HIV. In another embodiment, the target sequence corresponds to proviral DNA of an HIV. In some embodiments, the HIV is HIV-1 group M.

In another embodiment, the present invention provides a method for amplifying a target sequence, the method comprising: performing a PCR with the target sequence as template, wherein performing comprises providing the PCR with a forward primer comprising the sequence as set forth in SEQ ID NO:3 and a reverse primer comprising the sequence as set forth in SEQ ID NO:4. In one embodiment, the target sequence corresponds to cDNA prepared from RNA of a sample comprising an HIV. In another embodiment, the target sequence corresponds to proviral DNA of an HIV. In some embodiments, the HIV is HIV-1 group O.

In one embodiment, the present invention provides a method for amplifying a target sequence, the method comprising: performing a PCR with the target sequence as template, wherein performing comprises providing the PCR with a forward primer comprising the sequence as set forth in SEQ ID NO:5 and a reverse primer comprising the sequence as set forth in SEQ ID NO:6. In one embodiment, the target sequence corresponds to cDNA prepared from RNA of a sample comprising an HIV. In another embodiment, the target sequence corresponds to proviral DNA of an HIV. In some embodiments, the HIV is HIV-2.

In other embodiments, the present invention provides a method for amplifying a target sequence, the method comprising: performing a PCR with the target sequence as template, wherein performing comprises providing the PCR with a first forward primer comprising the sequence as set forth in SEQ ID NO:1, a first reverse primer comprising the sequence as set forth in SEQ ID NO:2, a second forward primer comprising the sequence as set forth in SEQ ID NO:3, and a second reverse primer comprising the sequence as set forth in SEQ ID NO:4. In one embodiment, the target sequence corresponds to cDNA prepared from RNA of a sample comprising an HIV. In another embodiment, the target sequence corresponds to proviral DNA of an HIV. In some embodiments, the HIV is HIV-1 group M and/or HIV-1 group O.

In other embodiments, the present invention provides a method for amplifying a target sequence, the method comprising: performing a PCR with the target sequence as template, wherein performing comprises providing the PCR with a first forward primer comprising the sequence as set forth in SEQ ID NO:1, a first reverse primer comprising the sequence as set forth in SEQ ID NO:2, a second forward primer comprising the sequence as set forth in SEQ ID NO:5, and a second reverse primer comprising the sequence as set forth in SEQ ID NO:6. In one embodiment, the target sequence corresponds to cDNA prepared from RNA of a sample comprising an HIV. In another embodiment, the target sequence corresponds to proviral DNA of an HIV. In some embodiments, the HIV is HIV-1 group M and/or HIV-2.

In other embodiments, the present invention provides a method for amplifying a target sequence, the method comprising: performing a PCR with the target sequence as template, wherein performing comprises providing the PCR with a first forward primer comprising the sequence as set forth in SEQ ID NO:3, a first reverse primer comprising the sequence as set forth in SEQ ID NO:4, a second forward primer comprising the sequence as set forth in SEQ ID NO:5, and a second reverse primer comprising the sequence as set forth in SEQ ID NO:6. In one embodiment, the target sequence corresponds to cDNA prepared from RNA of a sample comprising an HIV. In another embodiment, the target sequence corresponds to proviral DNA of an HIV. In some embodiments, the HIV is HIV-1 group O and/or HIV-2.

In other embodiments, the present invention provides a method for amplifying a target sequence, the method comprising: performing a PCR with the target sequence as template, wherein performing comprises providing the PCR with a first forward primer comprising the sequence as set forth in SEQ ID NO:1, a first reverse primer comprising the sequence as set forth in SEQ ID NO:2, a second forward primer comprising the sequence as set forth in SEQ ID NO:3, a second reverse primer comprising the sequence as set forth in SEQ ID NO:4, a third forward primer comprising the sequence as set forth in SEQ ID NO:5, and a third reverse primer comprising the sequence as set forth in SEQ ID NO:6. In one embodiment, the target sequence corresponds to cDNA prepared from RNA of a sample comprising an HIV. In another embodiment, the target sequence corresponds to proviral DNA of an HIV. In some embodiments, the HIV is HIV-1 group M, HIV-1 group O, and/or HIV-2.

In other aspects, the present invention provides a method for determining HIV in a sample. For example, the sample can comprise HIV RNA and/or proviral DNA or the sample may be suspected of comprising the same.

In one embodiment, the present invention provides a method for determining HIV in a sample, the method comprising:
(a) performing a PCR with a nucleic acid template in the sample using a forward primer comprising the sequence as set forth in SEQ ID NO:1 and a reverse primer comprising the sequence as set forth in SEQ ID NO:2; and
(b) detecting an amplicon generated by the forward and the reverse primer, wherein the presence of the amplicon determines the HIV in the sample.

In one embodiment, the template is a cDNA prepared from RNA of a sample comprising an HIV. In another embodiment, the template comprises proviral DNA of an HIV.

In some embodiments, the HIV is an HIV-1 group M. In one embodiment, the HIV-1 group M has a nucleic acid sequence as disclosed by, e.g., GENBANK Accession Nos. AF033819, AY173953, or AY214024, each of which is herein incorporated by reference in its entirety.

In other embodiments, the forward primer comprises the sequence as set forth in SEQ ID NO:3 and the reverse primer comprises the sequence as set forth in SEQ ID NO:4. In one embodiment, the HIV is an HIV-1 group O. In another embodiment, the HIV-1 group O has a nucleic acid sequence as disclosed by, e.g., GENBANK Accession Nos. AY169802, AB485669.1, or GQ351296.2, each of which is herein incorporated by reference in its entirety.

In other embodiments, the forward primer comprises the sequence as set forth in SEQ ID NO:5 and the reverse primer comprises the sequence as set forth in SEQ ID NO:6. In one embodiment, the HIV is an HIV-2. In another embodiment, the HIV-2 has a nucleic acid sequence as disclosed by, e.g., GENBANK Accession Nos. X52223, AJ011222.1, each of which is herein incorporated by reference in its entirety.

The step of detecting can be performed by a number of techniques known to one of ordinary skill in the art. In one embodiment, the amplicon can be detected using a probe that is labeled for detection and can be directly or indirectly hybridized with the amplicon. The probe may be soluble or attached to a solid support.

In one embodiment, the probe comprises a detectable label corresponding to a donor/acceptor pair suitable for detecting using FRET, wherein the probe comprises a sequence as set forth in SEQ ID NO:7, SEQ ID NO:8, SEQ ID NO:9, or complements thereof. For example, in some embodiments, the donor/acceptor pair is FAM/BHQ-1.

In another embodiment, one or more of the primers used to amplify the target nucleic acid can be labeled, for example, with a specific binding moiety. The resulting primer extension product into which the labeled primer has been incorporated can be captured with a probe. Detection of the amplified target hybridized to the probe can be achieved by detecting the presence of the labeled probe or labeled amplified target using suitable detection equipment and procedures that are well known in the art.

In other embodiments, one or more of the primers used to amplify the target nucleic acid is labeled with biotin and the biotinylated amplified target nucleic acids are hybridized to probes attached to a solid support. The bound targets are then detected by contacting them with a streptavidin-peroxidase conjugate in the presence of an oxidant, such as hydrogen peroxide, and a suitable dye-forming composition.

Other techniques are known to one of ordinary skill in the art for detecting including, but not limited to, methods involving southern blotting, dot blot techniques, or nonisotopic capture detection with a labeled probe.

In other embodiments, the present invention provides a method for determining HIV-1 group M, HIV-1 group O, and/or HIV-2 in a sample, the method comprising:

(a) performing a single PCR with the sample using (i) a first forward primer comprising the sequence as set forth in SEQ ID NO:1 and a first reverse primer comprising the sequence as set forth in SEQ ID NO:2; (ii) a second forward primer comprising the sequence as set forth in SEQ ID NO:3 and a second reverse primer comprising the sequence as set forth in SEQ ID NO:4; and (iii) a third forward primer comprising the sequence as set forth in SEQ ID NO:5 and a third reverse primer comprising the sequence as set forth in SEQ ID NO:6; and (b) detecting an amplicon generated by (i) the first forward and the first reverse primers, (ii) the second forward and the second reverse primers, and/or (iii) the third forward and the third reverse primers, wherein the presence of the amplicon determines the HIV in the sample.

In one embodiment, the step of detecting comprises including in the PCR an oligonucleotide probe comprising a detectable label corresponding to a donor/acceptor pair suitable for detecting using FRET, wherein the probe comprises a sequence as set forth in SEQ ID NO:7, SEQ ID NO:8, SEQ ID NO:9, or complements thereof. For example, in some embodiments, the donor/acceptor pair is FAM/BHQ-1.

In another embodiment, the step of detecting comprises including in the PCR a first probe comprising a sequence as set forth in SEQ ID NO:7, a second probe comprising a sequence as set forth in SEQ ID NO:8, and a third probe comprising a sequence as set forth in SEQ ID NO:9. In one embodiment, the first, the second, and the third probe each comprise the same donor/acceptor pair as label. For example, the donor/acceptor pair can be, but is not limited to, FAM/BHQ-1. In another embodiment, the first, the second, and the third probe each comprise different donor/acceptor pairs as label.

Thus, the nucleic acid molecules of the present invention can be employed singly or in combination in a variety of methods for amplifying and/or determining HIV. Accordingly, in some embodiments, the compositions, methods, and kits of the present invention provide for multiplex real time PCR assay that comprise one, two, or three sets of primers and probes as described herein, each specific for one HIV target, in the same PCR master mix. For example, a multiplex real time PCR assay in accordance with the present invention can detect 3 HIV genotypes (i.e., HIV-1 group M, HIV-1 group O, HIV-2) using a single test. In this regard, the primers and probes are capable of interacting only with their specific target and not with other primers and probes present in the master mix (e.g., do not form primer-dimers) thereby providing for efficient target amplification and detection in PCR, e.g., multiplex PCR.

In other aspects, the present invention provides a kit comprising the isolated nucleic acid molecules including the primers and probes of the present invention. The kit can be developed using the nucleic acid sequences disclosed herein. These sequences can be used as primers in nucleic acid amplification reactions, and/or as probes in a nucleic acid hybridization method. The kits are useful for determining the presence of a HIV, in particular HIV-1 group M, HIV-1 group O, and/or HIV-2 nucleic acid sequence in a sample. Components in the kit can either be obtained commercially or made according to well-known methods in the art. In addition, the components of the kit can be in solution or lyophilized as appropriate. In one embodiment, the components are in the same compartment, and in another embodiment, the components are in separate compartments. In some embodiments, the kit further comprises instructions for use.

In one embodiment, the kit comprises a forward primer, a reverse primer, and a probe, wherein the forward primer comprises a forward primer nucleic acid sequence as set forth in (SEQ ID NO:1), (SEQ ID NO:3), or (SEQ ID NO:5), wherein the reverse primer comprises a reverse primer nucleic acid sequence as set forth in (SEQ ID NO:2), (SEQ ID NO:4), or (SEQ ID NO:6), wherein the probe comprises a probe nucleic acid sequence as set forth in (SEQ ID NO:7), (SEQ ID NO:8), (SEQ ID NO:9), or a complement thereof.

In another embodiment, the kit comprises a first primer pair for use in combination with a first probe for determining HIV-1 group M, a second primer pair for use in combination with a second probe for determining HIV-1 group O, and a third primer pair for use in combination with a third probe for determining HIV-2, wherein the first primer pair comprises the sequence as set forth in (SEQ ID NO:1/SEQ ID NO:2), wherein the first probe comprises the sequence as set forth in SEQ ID NO:7, wherein the second primer pair comprises the sequence as set forth in (SEQ ID NO:3/SEQ ID NO:4), wherein the second probe comprises the sequence as set forth in SEQ ID NO:8, wherein the third primer pair comprises the sequence as set forth in (SEQ ID NO:5/SEQ ID NO:6), wherein the third probe comprises the sequence as set forth in SEQ ID NO:7.

The following examples are provided for illustration only.

EXAMPLES

Example 1

Determining HIV by Multiplex PCR

To determine the presence of HIV RNA in a plasma sample, a simultaneous PCR assay was performed using primers and probes whereby the primers provided for amplification of a cDNA template prepared from HIV-1 group M, HIV-1 group O, and/or HIV-2 RNA that may be present in the sample, and the resulting amplicons were detected in real time by the hybridization of amplicon-specific probes that were labeled for detection by FRET.

Three compatible primer/probe sets were selected to ensure efficient amplification and detection of HIV-1 group M, HIV-1 group O, and/or HIV-2 RNA. Each detection probe comprises a FAM (donor) at the 5'-end; and a BHQ-1 (acceptor) at the 3'-end.

For determining the presence of HIV-1 group M in the sample, primers and detection probe having the following sequences were employed:

```
Forward Primer:
                                    (SEQ ID NO: 1)
  5'-GAC ATC AAG CAG CCA TGC AAA T-3';

Reverse Primer:
                                    (SEQ ID NO: 2)
  5'-AGT AGT TCC TGC TAT GTC ACT TC-3';

Probe:
                                    (SEQ ID NO: 7)
  5'-ACC ATC AAT GAG GAA GCT GCA GAA TGG GAT-3'.
```

For determining the presence of HIV-1 group O in the sample, primers and probe having the following sequences were employed:

Forward Primer:
(SEQ ID NO: 3)
5'-GAG GAC ATC AAG GGG CTT TAC A-3';

Reverse Primer:
(SEQ ID NO: 4)
5'-CAG CAA TGT CAC TTC CTG TTG-3';

Probe:
(SEQ ID NO: 8)
5'-TCC CTT ATC TGC CCT GGT GGT AAC GG-3'.

For determining the presence of HIV-2 in the sample, primers and probe having the following sequences were employed:

Forward Primer:
(SEQ ID NO: 5)
5'-GGC AGA GGT AGT GCC AG-3';

Reverse Primer:
(SEQ ID NO: 6)
5'-GGT CGC CCA CAC AAT TAA GC-3';

Probe:
(SEQ ID NO: 9)
5'-AGG CAC TCT CAG AAG GCT GCA CG-3'.

A multiplex PCR master mix (MMX) was prepared comprising the following: 1×PCR buffer (50 mM Bicine, 115 mM Potassium acetate, 8% glycerol, pH 8.2) (a Tris-based buffer may alternatively be used); 300 µM dNTPs; 3% DMSO; 3.5 mM $MgCl_2$; 1×ROX reference dye (0.5 µM); 100 nM HIV-1 group M forward primer; 300 nM HIV-1 group M reverse primer; 100 nM HIV-1 group M probe; 100 nM HIV-1 group O forward primer; 300 nM HIV-1 group O reverse primer; 100 nM HIV-1 group O probe; HIV-2 forward primer; HIV-2 reverse primer; 100 nM HIV-2 probe; 100 nM Internal Control probe; 30 Units/reaction Reverse Transcriptase (RT); and 2.5 Units/reaction Taq DNA polymerase.

The MMX was combined with viral RNA isolated from plasma samples containing the virus using a virus extraction method known in the art. The combined HIV RNA+MMX was subjected to one-step PCR, where the reverse transcription, amplification of cDNA, and detection occurred in the same tube, using a commercial real time PCR instrument (Applied Biosystems 7300). The thermal cycling conditions are shown in Table 1:

TABLE 1

| PCR cycling conditions | | |
| --- | --- | --- |
| Temperature | Time | Cycles |
| 55° C. | 45 min | 1 |
| 95° C. | 2 min | 1 |
| 90° C. | 15 sec | 45 |
| 55° C. | 1 min | |

Following PCR amplification, the signals generated were analyzed using the instrument SDS software. The results show strong amplification curves with CT values lower than 40. Thus, we were able to detect all three HIV genotypes, HIV-1 group M, HIV-1 group O, and HIV-2, from spiked plasma samples. The three detection probes present in the assay were labeled with the same fluorescent dye in which case all three genotypes were detected but not differentiated. The three probes can be labeled with three different dyes for both detection and differentiation of the three HIV genotypes.

We claim:

1. A method for amplifying an HIV-1 group M, HIV-1 group O, and HIV-2 target sequence, the method comprising:
performing a single multiplex real time PCR with the HIV-1 group M, HIV-1 group O, and HIV-2 target sequences as templates, wherein performing comprises providing the PCR with forward primer and reverse primer pairs, wherein the forward primer and the reverse primer pairs consist of, respectively, the sequences as set forth in SEQ ID NO:1 and SEQ ID NO:2; SEQ ID NO:3 and SEQ ID NO:4; and SEQ ID NO:5 and SEQ ID NO:6.

2. The method of claim 1, wherein the target sequences corresponds to cDNA prepared from RNA of a sample comprising HIV-1 group M, HIV-1 group O, and HIV-2.

3. The method of claim 1, wherein the target sequences corresponds to proviral DNA of HIV-1 group M, HIV-1 group O, and HIV-2.

4. A method for detecting HIV-1 group M, HIV-1 group O, and HIV-2 in a sample, the method comprising:
(a) performing a single multiplex real time PCR with nucleic acids in the sample using:
(i) a first forward primer consisting of SEQ ID NO:1, a first reverse primer consisting of SEQ ID NO:2, and a first probe consisting of SEQ ID NO:7;
(ii) a second forward primer consisting of SEQ ID NO:3, a second reverse primer consisting of SEQ ID NO:4, and a second probe consisting of SEQ ID NO:8; and
(iii) a third forward primer consisting of SEQ ID NO:5, a third reverse primer consisting of SEQ ID NO:6, and a third probe consisting of SEQ ID NO:9; and
(b) detecting an amplicon generated by (i) the first forward and the first reverse primers, (ii) the second forward and the second reverse primers, and/or (iii) the third forward and the third reverse primers, whereby the amplicon, if present, contacts the first, second, and/or third probe.

5. The method of claim 4, wherein each probe is labeled with 6-carboxyfluorescein/N-(4-(4-(2-Nitro-4-methylphenylazo)-2-methoxy-5-methylphenylazo)-phenyl)-N,N-bis-(2-aminoethanol).

6. The method of claim 4 wherein the nucleic acids are cDNAs prepared from RNA of a sample comprising HIV.

7. The method of claim 4 wherein the nucleic acids comprise proviral DNA of an HIV-1 group M, HIV-1 group O, and HIV-2.

* * * * *

SEQUENCE LISTING

<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
gacatcaagc agccatgcaa at                                              22

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
agtagttcct gctatgtcac ttc                                             23

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

```
<400> SEQUENCE: 3
gaggacatca agggqcttta ca                                          22

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
cagcaatgtc acttcctgtt g                                           21

<210> SEQ ID NO 5
<211> LENGTH: 17
<212> TYPE: DNA
<213> ORGANISM: Artificial Sequence
<220> FEATURE:
<223> OTHER INFORMATION: Synthetic primer

<400> SEQUENCE: 5
ggcagaggta gtgccag                                                17

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
ggtcgcccac acaattaagc                                             20

<210> SEQ ID NO 7
<211> LENGTH: 30
<212> TYPE: DNA
<213> ORGANISM: Artificial Sequence
<220> FEATURE:
<223> OTHER INFORMATION: Synthetic primer

<400> SEQUENCE: 7
accatcaatg aggaagctgc agaatgggat                                  30

<210> SEQ ID NO 8
<211> LENGTH: 26
<212> TYPE: DNA
<213> ORGANISM: Artificial Sequence
<220> FEATURE:
<223> OTHER INFORMATION: Synthetic primer

<400> SEQUENCE: 8
tcccttatct gccctggtgg taacgg                                      26

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
aggcactctc agaaggctgc acg                                         23
```